(12) United States Patent
Mehdizadeh (10) Patent No.: US 8,818,820 B1
(45) Date of Patent: Aug. 26, 2014

(54) SYSTEM TO VERIFY IDENTITY OF PATIENT RECEIVING MEDICATION AND MONITORING THE DISPENSING OF MEDICATION TO THE PATIENT INCLUDING MONITORING THE DEVELOPMENT OF THE MEDICATION FORM WHERE THE SEEDS ARE OBTAINED, HOW THE PLANT WAS CULTIVATED, WHERE THE MEDICAL PORTION OF THE PLANT WAS HARVESTED AND CONVERTED INTO THE MEDICATION TO BE DISPENSED TO A PATIENT (75) Inventor: P. Vincent Mehdizadeh, West Hills, CA (US)

(73) Assignee: PVM International, Inc., West Hills, CA (US)

( * ) Notice: Subject to any disclaimer, the term of this patent is extended or adjusted under 35 U.S.C. 154(b) by 537 days.

(21) Appl. No.: 12/931,761

(22) Filed: Feb. 10, 2011

Related U.S. Application Data

(63) Continuation-in-part of application No. 12/925,508, filed on Oct. 22, 2010, now abandoned.

(60) Provisional application No. 61/337,978, filed on Feb. 11, 2010.

(51) Int. Cl.
*G06Q 50/22* (2012.01)
*G01N 33/94* (2006.01)

(52) U.S. Cl.
CPC ............ *G06Q 50/22* (2013.01); *A61K 2300/00* (2013.01); *G01N 33/948* (2013.01)
USPC ............................................................. 705/2

(58) Field of Classification Search
CPC .. G06Q 55/22; A61K 2300/00; G01N 33/948
USPC ............................................................. 705/2
See application file for complete search history.

(56) References Cited

U.S. PATENT DOCUMENTS

2010/0286993 A1* 11/2010 Lovelace ........................ 705/2

* cited by examiner

*Primary Examiner* — Shay S Glass
(74) *Attorney, Agent, or Firm* — Rozsa Law Group LC (57) ABSTRACT

A computer system to monitor and authenticate the creation of a medicinal herb including information on where seeds used to grow a plant containing a medicinal herb buds were obtained from, information on how and where the seeds were grown to cultivate the plant, information on when the buds were harvested from the plant and converted into a medicinal herb full chain a custody of all personnel involved from obtaining the seeds, cultivating the seeds into a plant, harvesting growth from the plant and converting it into a medicinal herb and transportation of the medicinal herb to a dispensing facility and how the medicinal herb was dispensed to a patient.

3 Claims, 10 Drawing Sheets

```
┌─────────────────────────────────────────────────────────────┐
│ Complete tracking of the evolution of the medicinal herb    │
│ before it ever gets to the location where the medicinal herb│
│ is dispensed.                                               │
└─────────────────────────────────────────────────────────────┘
                              ⇩
┌─────────────────────────────────────────────────────────────┐
│ A computer file is opened. The first step is obtaining      │
│ authentication information on where the seeds from which    │
│ the plant to grow the herbal medicine were obtained,        │
│ including information about the seed grower, the specific   │
│ type of special variety of plant seed, and a written chain  │
│ of custody from the seed grower to the location where the   │
│ seeds will be harvested. This information is entered into   │
│ the computer database.                                      │
└─────────────────────────────────────────────────────────────┘
                              ⇩
┌─────────────────────────────────────────────────────────────┐
│ Information about whether the seeds were feminized seeds to │
│ create only female plants or normal seeds creating both     │
│ female and male plants is entered into the computer database.│
└─────────────────────────────────────────────────────────────┘
                              ⇩
┌─────────────────────────────────────────────────────────────┐
│ In the computer file a record is kept setting forth detailed│
│ information about the seed grower, where the seeds were     │
│ germinated, the shipping documents to confirm the           │
│ authenticity of the specific seeds including the variety of │
│ herbal medicine to be obtained from the seed.               │
└─────────────────────────────────────────────────────────────┘
                              ⇩
┌─────────────────────────────────────────────────────────────┐
│ The authentication information about the seeds is entered   │
│ into a computerized database and the individual or          │
│ individuals at the cultivation facility are fingerprinted   │
│ when they are given possession of the seeds.                │
└─────────────────────────────────────────────────────────────┘
                              ⇩
┌─────────────────────────────────────────────────────────────┐
│ The seeds are placed in a sealed packet with a specific seed│
│ identification number placed on the packet.                 │
└─────────────────────────────────────────────────────────────┘
```

The information on the packaging of the dried and cured harvested bud is entered into the computer database including placing the identification number on the packet containing the dried and harvested buds, the identity of the individual who packaged the dried and cured harvested buds and the shipping information on which shipper, shipping method, invoice, bill of lading and other shipping information of how the packaged dried and cured buds were shipped to the dispensing facility is entered into the computer database.

FIG. 10

The identity of the individual who received the package of the dried and cured buds at the dispensing facility and complete chain of handling from opening the container in which the package was shipped and into which dispensing medium such as a specific vending machine including the identification number on the packaging containing the dried and cured buds and the identification number of the dispensing medium such as vending machine is recorded in the computer database.

SYSTEM TO VERIFY IDENTITY OF PATIENT RECEIVING MEDICATION AND MONITORING THE DISPENSING OF MEDICATION TO THE PATIENT INCLUDING MONITORING THE DEVELOPMENT OF THE MEDICATION FORM WHERE THE SEEDS ARE OBTAINED, HOW THE PLANT WAS CULTIVATED, WHERE THE MEDICAL PORTION OF THE PLANT WAS HARVESTED AND CONVERTED INTO THE MEDICATION TO BE DISPENSED TO A PATIENT

The present invention is a continuation-in-part of patent application Ser. No. 12/925,508 filed on Oct. 22, 2010 now abandoned which claims priority to Provisional Patent Application Ser. No. 61/337,978 filed on Feb. 11, 2010.

BACKGROUND OF THE INVENTION

1. Field of the Invention

The present invention relates to a computer software system and method of monitoring medication dispensed to a patient from a retail establishment such as a pharmacy and verifying the identity of the patient to whom the medication is dispensed and whether the patient's authorization to acquire the medication has not expired.

The present invention also relates to a computer software system to fully monitor the entire process of creation of the medication to verify authenticity of the medication.

2. Description of the Prior Art

To the best of the present inventor's knowledge, there is no system comparable to the present invention which is available on the market.

SUMMARY OF THE INVENTION

The present invention is a point-of-sale system that is used at pharmacies and other retail outlets where the identity of the individual purchasing medication needs to be verified. In one embodiment, the system incorporates magnetic swipe cards that have refillable monetary amounts that are deducted every time the patient is dispensed medication. The system also incorporates fingerprint verification to insure the correct patient's identity as well as determine whether the patient's physician's statement to acquire the medication has not expired. The system will allow retail operators to track inventory as well as demonstrate compliance with local and state laws regarding dispensing medications including herbal medications.

In some situations, there is no monitoring of the amount of times a patient uses a prescription for an herbal medication. In some cases, patients have abused the system by obtaining refills for prescription herbal medications at numerous different pharmacies or other retail establishments which are licensed to fill prescriptions for herbal medications. The present invention provides a software system to accumulate the number of prescription refills used by a patient over a period of time such as a month, two months, six months, etc. and a given geographic area such as a town, section of a city, a city, a state, etc., and transmit that information to a central database where the information is processed to determine if the patient is properly using the prescription to obtain only the prescribed amount of herbal medication allotted for a given period of time. The information is sent by e-mail reports or comparable secure transmission methods at the end of the given period of time to a central database which is controlled by law enforcement, medical boards, or other authorized authorities to confirm proper usage of the herbal prescription by the patient and to intervene and stop abuse of the system.

It is an object of the present invention to provide a point-of-sale system that is used at pharmacies and other retail outlets where the identity of the individual purchasing medication, including herbal medication, needs to be verified.

It is another object of the present invention to provide a system which incorporates magnetic swipe cards that have refillable monetary amounts that are deducted every time the patient is dispensed medication.

It is a further object of the present invention to provide a system which also incorporates fingerprint verification to insure that the identify of the patient is correct before the medication is dispensed to the patient.

It is an additional object of the present invention to allow retail operators to track inventory as well as demonstrate compliance with local and state laws regarding dispensing medications including herbal medications.

It is also an object of the present invention to monitor the usage of an herbal prescription by an individual to be sure that the individual is properly using the prescription and not abusing the system by obtaining refills for a prescription at different authorized dispensing outlets which are not in communication with each other. The system transmits all herbal prescription refill usage by a person over a period of time in a selected region to a central database monitored by authorities such as police to confirm compliance by the individual using only the authorized amount of prescription herbal medicine refills and intervening and stopping any abuse of the system by the individual using the prescription to obtain an unauthorized number of refills at different dispensing locations.

The present invention is also a computer system to fully monitor and authenticate the creation of the medicinal herb including monitoring where the seeds used to grow the plant were obtained from, how and where the seeds were grown to cultivate a plant from which the medicinal herb was harvested and the process by which the harvested portion of the plant was converted into a medicinal herb. The process includes full chain of custody of all personnel involved from obtaining the seeds, cultivating the plant, harvesting the plant and converting the harvested plant into a medicinal herb and transportation of the medicinal herb to a legal dispensary.

It is an object of the present invention to provide a full authentication and verification process to verify that the medicinal herb was obtained from legally cultivated seeds, the cultivation was conducted in strict compliance with all applicable laws, the harvested portion of the plant was properly obtained and the process of converting the harvested portion of the plant into the medical herb was done in compliance with all applicable laws.

It is a further object of the present invention to provide a full chain of custody from obtaining the seeds through supplying the medicinal herbs to be certain that the medicinal herbs being dispensed to a patient was obtained in strict compliance with all applicable laws.

It is an additional object the present invention to provide a system for monitoring the growing of the medicinal herb at a cultivation facility and providing a biometric chain of custody from the time the medicinal herb is grown until it is brought to a clinic for dispensing to patient.

It is a key object of the present invention to track the evolution of the medicinal herb from immature plant to harvested medicinal herb. All employees and independent contractors would need to log into the system through fingerprint and every step of the process from "seed to sale" is monitored.

It is an object of the present invention to provide a method of authentication and verification of a medicinal herb comprising:
  a. obtaining authentication information on where seeds from which a plant to grow the medicinal herb were obtained, including legal seed selling information about the seed grower, the specific type of special variety of plant seed, and a written chain of custody from the seed grower to the location where the seeds will be grown into plants which is then entered into a computer database;
  b. obtaining information about whether the seeds were feminized seeds to create only female plants or normal seeds creating both female and male plants, which information is entered into the computer database;
  c. keeping a computer database record setting forth detailed information about the seed grower, where the seeds were germinated and the shipping documents to confirm the authenticity of the specific seeds including the variety of medicinal herb to be obtained from the seeds;
  d. entering into the computer database the name, home address and fingerprint information about an individual or individuals who are given possession of the seeds when the seeds arrive at a cultivation facility to grow the seeds into plants, and inputting information on a packet into which the seeds are placed including a specific seed identification number placed on the packet;
  e. obtaining additional information about the soil used to grow the seeds into plants, the type of grow light used, and nutrients added to the soil, which information is entered into the computer database;
  f entering into the computer database the location of the cultivation facility and the employees who are in charge of growing the seeds into a plant, the computer database including information about the growing facility, its license to grow the medicinal herb, and the specific greenhouse number where the seeds will be grown into a plant;
  g. entering into the computer database information on the identification of the employee who planted the seeds into a pot, a label placed on the pot with a corresponding identification number obtained from the packet into which the seeds were placed when they arrived at the cultivation facility from the seed grower;
  h. entering into the computer database growing information setting forth when the plant began to sprout and the rate of growth of the plant, when the plant began to flower and when herbal buds began to form;
  i. entering into the computer database the day, date and time when the herbal buds from the plant were trimmed and harvested, including the identity of the individual who did the harvesting, information about when the plant was cut and where the herbal buds were removed from the plant;
  j. entering into the computer database information including pictures of the trimmed herbal buds, how the harvested buds were dried and cured including the identity of the individual who dried and cured the herbal buds and information on how the herbal buds were treated to become a medicinal herb;
  k. entering into the computer database information on the packaging of the dried and cured harvested herbal buds including the corresponding identification number placed on a packet containing the dried and cured herbal buds which have been treated to become the medicinal herb, the identity of the individual who packaged the medicinal herb and the shipping information on which shipper, shipping method, invoice, bill of lading and other shipping information of how the medicinal herb was placed in a container and shipped to a dispensing facility;
  l. entering into the computer database the identity of the individual who received the package of the dried and cured buds at the dispensing facility and complete chain of handling from opening the container in which the package was shipped and into which dispensing medium the medicinal herb was placed including the identification number on the packaging containing the medicinal herb and an identification number of the dispensing medium; and
  m. entering into the computer database the day, date and time the medicinal herb was dispensed to a person.

It is also an object of the present invention to provide a method of authentication and verification of a medicinal herb comprising:
  a. obtaining authentication information on where seeds from which a plant to grow the medicinal herb were obtained including information about the seed grower, and entering into a computer database a written chain of custody from the seed grower to the location where the seeds will be grown into plants;
  b. keeping a computer database record setting forth detailed information about shipping documents to confirm the authenticity of the specific seeds including the variety of medicinal herb to be obtained from the seeds;
  c. entering into the computer database the personal and fingerprint information about an individual who is given possession of the seeds when the seeds arrive at a cultivation facility to grow the seeds into a plant, and inputting information on a packet into which the seeds are placed including a specific seed identification number placed on the packet;
  d. entering into the computer database the location of the cultivation facility and the employees who are in charge of growing the seeds into a plant, the computer database including information about the growing facility, its license to grow the medicinal herb, and the specific greenhouse number where the seeds will be grown into a plant;
  e. entering into the computer database information on the identification of the employee who planted the seeds into a pot, a label placed on the pot with a corresponding identification number obtained from the packet into which the seeds were placed when they arrived at the cultivation facility from the seed grower;
  f. entering into the computer database growing information on when the plant began to sprout herbal buds and when the herbal buds were harvested, including the identity of the individual who did the harvesting and a chain of custody information of how the herbal buds were converted into a medicinal herb and which individual performed transforming the herbal buds into a medicinal herb;
  g. entering into the computer database information on the packaging of the medicinal herb including the corresponding identification number placed on a packet containing the medicinal herb, the identity of the individual who packaged the medicinal herb and shipping from the cultivation facility to a dispensing facility;
  h. entering into the computer database the identity of the individual who received the medicinal herb at the dispensing facility and complete chain of handling from opening a container in which the package was shipped and into which dispensing medium the medicinal herb was placed including the identification number on the packaging containing the medicinal herb and an identification number of the dispensing medium; and i. entering into the computer database information on how and when the medicinal herb was dispensed to a person.

It is a further object of the present invention to provide a system comprising:

a. a computer system to monitor and authenticate the creation of a medicinal herb including information on where seeds used to grow a plant containing a medicinal herb buds were obtained from, information on how and where the seeds were grown to cultivate the plant, information on when the buds were harvested from the plant and converted into a medicinal herb; and b. computerized information including a full chain a custody of all personnel involved from obtaining the seeds, cultivating the seeds into a plant, harvesting growth from the plant and converting it into a medicinal herb and transportation of the medicinal herb to a dispensing facility and how the medicinal herb was dispensed to a patient.

It is additionally an object of the present invention to provide a system comprising a computerized database tracking evolution of a medicinal herb from seeds to immature plant to harvested plant material converted into a medicinal herb to verify that the medicinal herb being dispensed to a patient was obtained following all legal requirements from seed planting to dispensing of the medicinal herb.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
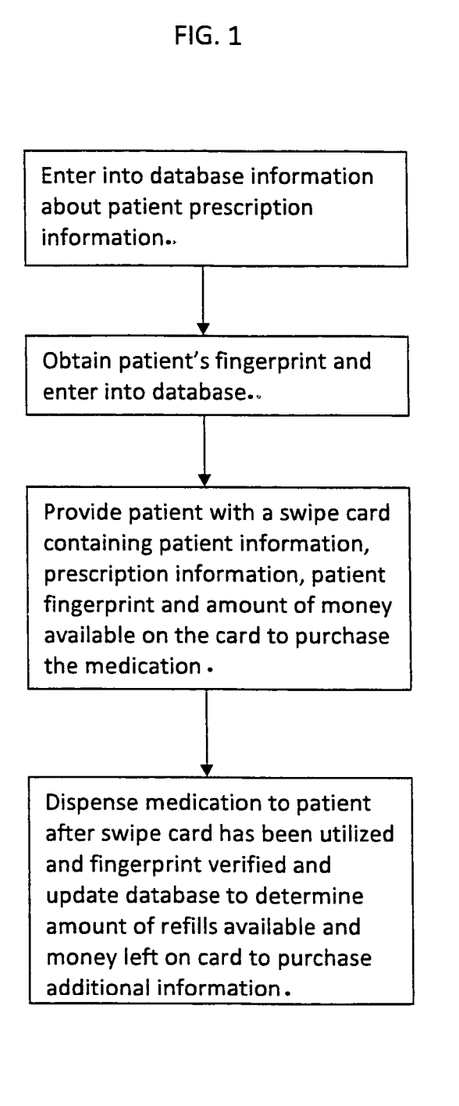
FIG. 1 is a block diagram illustrating the steps in the present invention system at a location authorized to dispense prescription herbal medications.

Referring to the first block step in FIG. 1, the first step in the present invention system is software which enables an employee of a retail establishment such as a pharmacy to register the individual who is a patient for herbal medications into the retail establishment's system using a computer based application that asks for and enters into the system specific information about the patient including the patient's name, date of birth, state identification number, prescription information including the name of the patient's treating physician, the physician's license number and the expiration date of the prescription. In addition, the amount of money credited to the patient's card is also entered. As an example, a newly registered patient may choose to put $100.00 on the card.

Referring to the second and third block steps in FIG. 1, once the patient is included in the database, fingerprint samples are taken. One method to take the patient's fingerprint is through a biometric reader that is plugged into a USB port of the computer. A separate USB port is utilized by a card reader that programs and encodes the patient's information and fingerprint sample on the registration card that is given to the patient.

Referring to the fourth block step in FIG. 1, once the patient has the registration card, the patient may use the registration card at the retail establishment such as a pharmacy by sliding the card through the card reader and placing the patient's finger on the biometric reader to confirm the patient's identity. The retail establishment's employee such as a technician at the pharmacy will then input the amount of medicine purchased and the amount charged to the patient, which will automatically be deducted from the patient's credit card account once the transaction is processed. A receipt will be printed out from an attached printer detailing the balance left on the patient's card to pay for the future medications.

Figure 2:
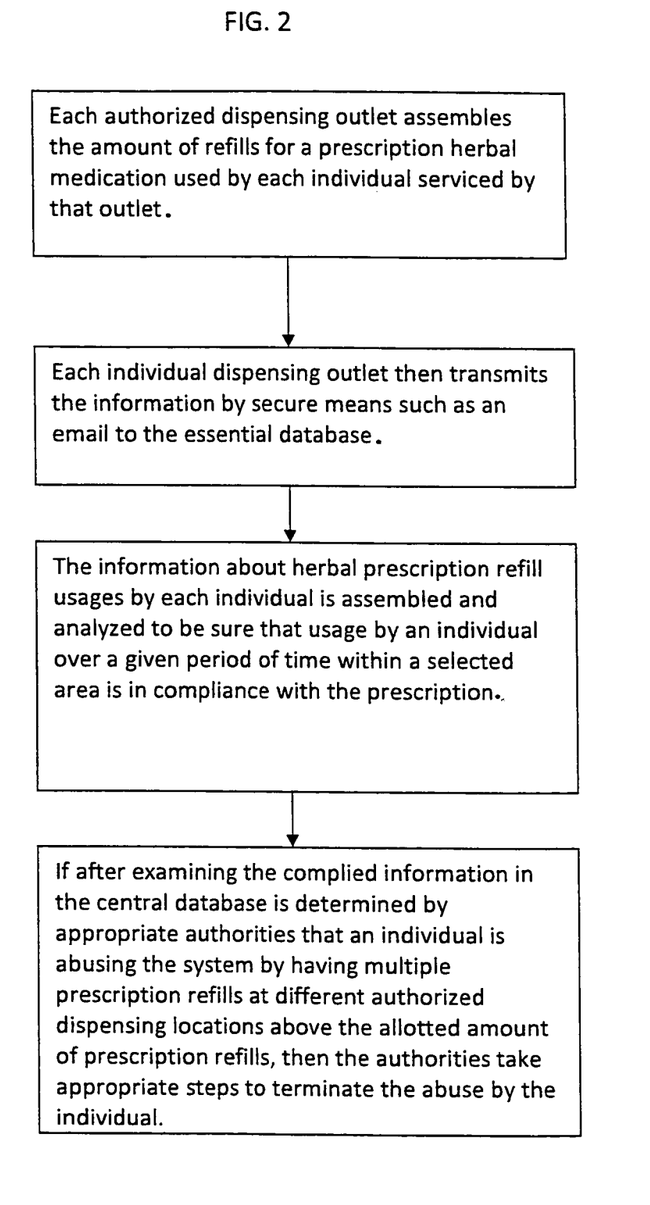
FIG. 2 is a block diagram illustrating the system transmitting information about a person's usage to a central database so that usage is monitored to be sure that the person is obtaining only the authorized amount of refills for a given period of time.

Referring to FIG. 2, there is illustrated the monitoring feature of the present invention. Referring to the first block step in FIG. 2, each authorized dispensing outlet assembles the amount of refills for a prescription herbal medication used by each individual serviced by that outlet and then transmits the information by secure means such as e-mail to a central database. Referring to the second block step in FIG. 2, the information about herbal prescription refill usage by each individual is assembled and analyzed to be sure that usage by an individual over a given period of time such as a month, two months, six months, etc. in a selected area such as a town, part of a city, city or state is in compliance with the prescription.

Referring to the third block step in FIG. 2, if after examining the compiled information in the central database it is determined by the appropriate authorities such as law enforcement that an individual is abusing the system by having multiple prescription refills at different authorized dispensing locations above the allotted amount of prescription refills, then the authorities take appropriate steps to terminate the abuse by the individual.

Therefore, through the present invention, a system is provided to track a patient's use of prescribed medication including herbal medications and to monitor how often a refill is requested as well as confirm that the patient to whom the medication is dispensed is in fact the correct individual who was issued the prescription. In addition, the system insures that medication will be promptly paid for when it is given to the patient.

The present invention also includes complete tracking of the evolution of the medicinal herb before it ever gets to the location where the medicinal herb is dispensed.

Figure 3:
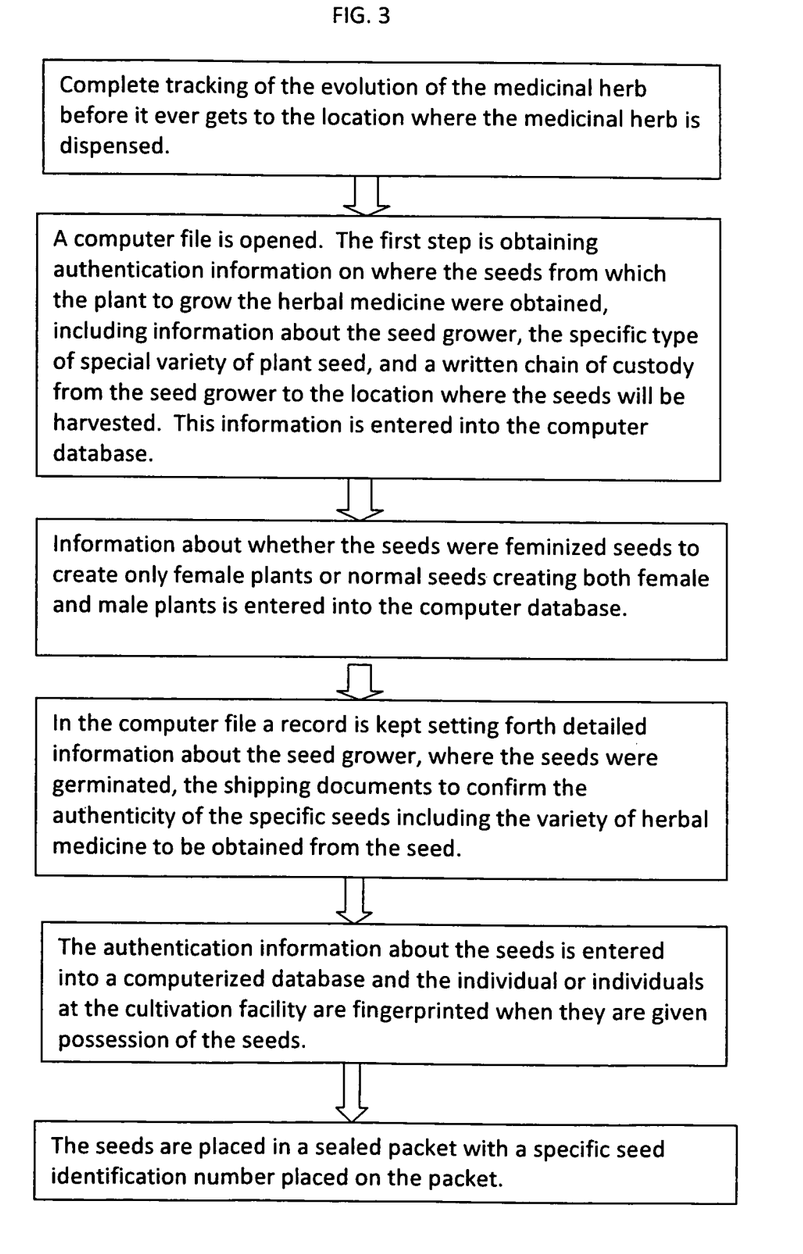
FIG. 3 is a block diagram illustrating the first steps for complete tracking of the evolution of a medicinal herb from growth to dispensing including authentication information about the seeds used to grow the plant from which the medicinal herb was obtained.

Referring to 3, a computer file is opened. The first step is obtaining authentication information on where the seeds from which the plant to grow the herbal medicine were obtained, including information about the seed grower, the specific type of special variety of plant seed, and a written chain of custody from the seed grower to the location where the seeds will be harvested. This information is entered into the computer database. Information about whether the seeds were feminized seeds to create only female plants or normal seeds creating both female and male plants is entered into the computer database. In the computer file a record is kept setting forth detailed information about the seed grower, where the seeds was germinated, the shipping documents to confirm the authenticity of the specific seeds including the variety of herbal medicine to be obtained from the seed.

The authentication information about the seeds is entered into a computerized database and the individual or individuals at the cultivation facility are fingerprinted when they are given possession of the seeds. The seeds are placed in a sealed packet with a specific seed identification number placed on the packet.

Figure 4:
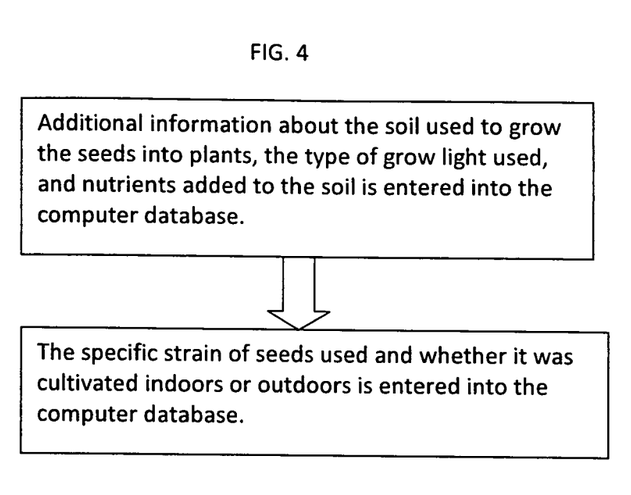
FIG. 4 is a block diagram showing information about the cultivation of the seeds.

Referring to FIG. 4, additional information about the soil used to grow the seeds into plants, the type of grow light used, and nutrients added to the soil is entered into the computer database. The specific strain of seeds used and whether it was cultivated indoors or outdoors is entered into the computer database.

Figure 5:
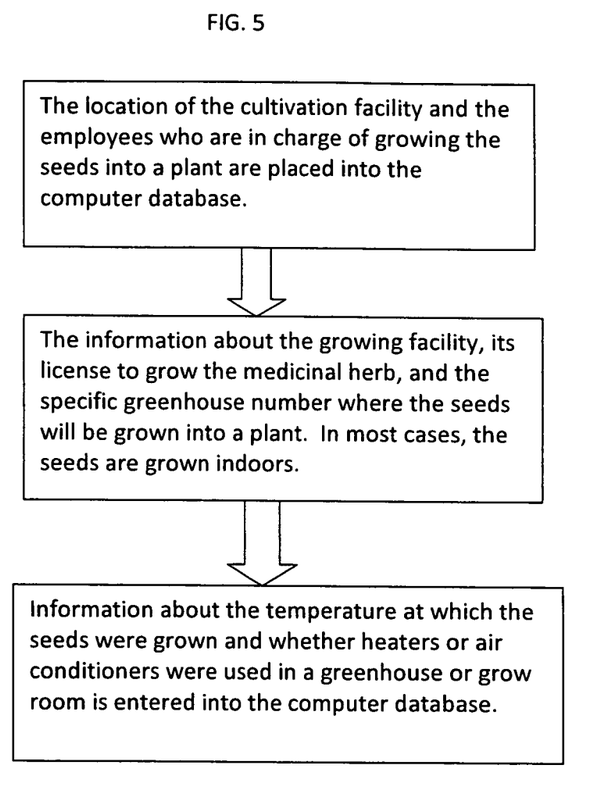
FIG. 5 is block diagram illustrating information about the cultivation facility and personnel who grew the seeds into a plant.

Referring further to FIG. 5, the location of the cultivation facility and the employees who are in charge of growing the seeds into a plant are placed into the computer database. The database includes information about the growing facility, its license to grow the medicinal herb, and the specific greenhouse number where the seeds will be grown into a plant. In most cases, the seeds are grown indoors. Information about the temperature at which the seeds were grown and whether heaters or air conditioners were used in a greenhouse or grow room is also entered into the computer database.

Figure 6:
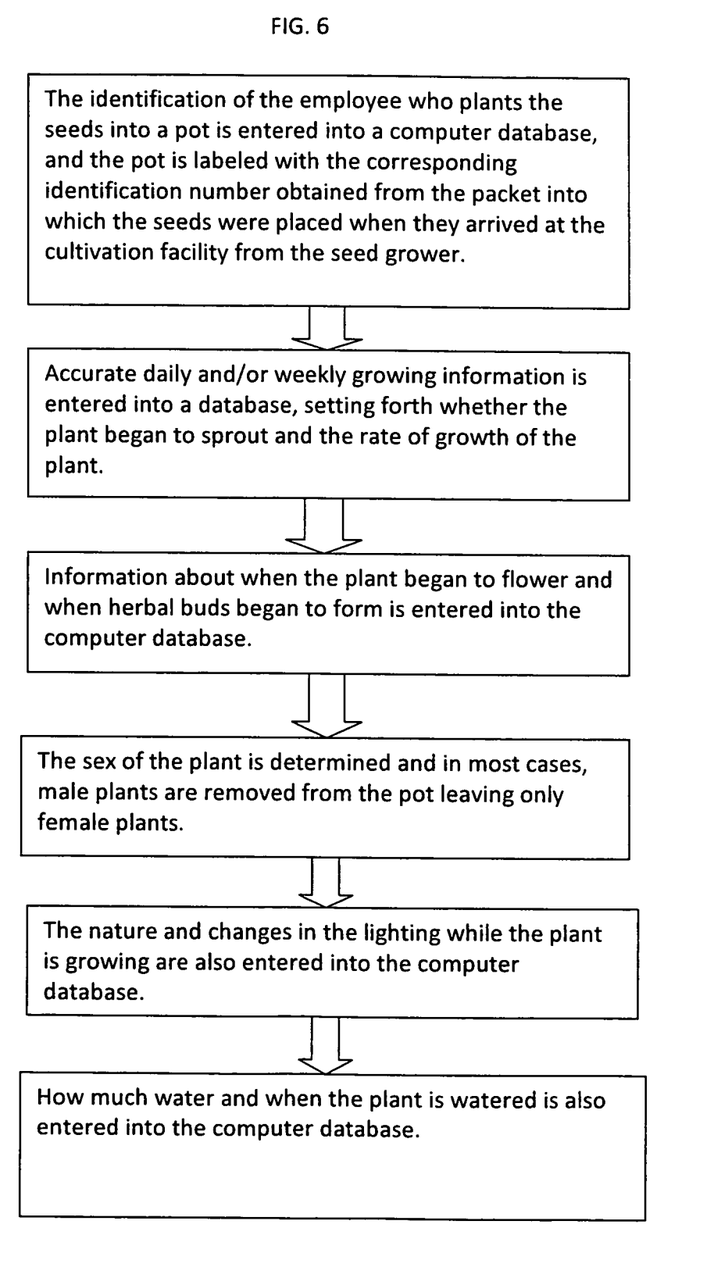
FIG. 6 is a block diagram illustrating the growth of the plant.

Referring to FIG. 6, the identification of the employee who plants the seeds into a pot is entered into a computer database and the pot is labeled with the corresponding identification number obtained from the packet into which the seeds were placed when they arrived at the cultivation facility from the seed grower.

Accurate daily and/or weekly growing information is entered into a database, setting forth whether the plant began to sprout and the rate of growth of the plant. Information about when the plant began to flower and where herbal buds began to form is entered into the computer database. The sex of the plant is determined and in most cases, male plants are removed from the pot, leaving only female plants. The nature and changes in the lighting while the plant is growing are also entered into the computer database. How much water and when the plant is watered are also entered into the computer database.

Figure 7:
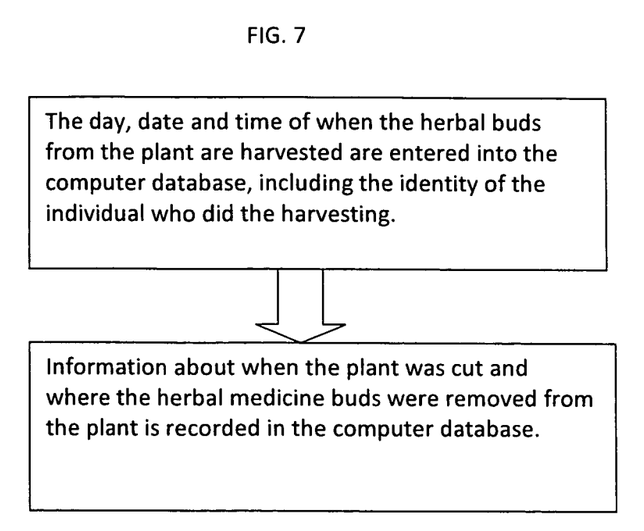
FIG. 7 is a block diagram illustrating information on the herbal medicinal buds from the plant.

Referring to FIG. 7, the day, date and time when the herbal buds from the plant are harvested is entered into the computer database, including the identity of the individual who did the harvesting. Information about when the plant was cut and where the herbal medicine buds were removed from the plant is recorded in the computer database.

Figure 8:
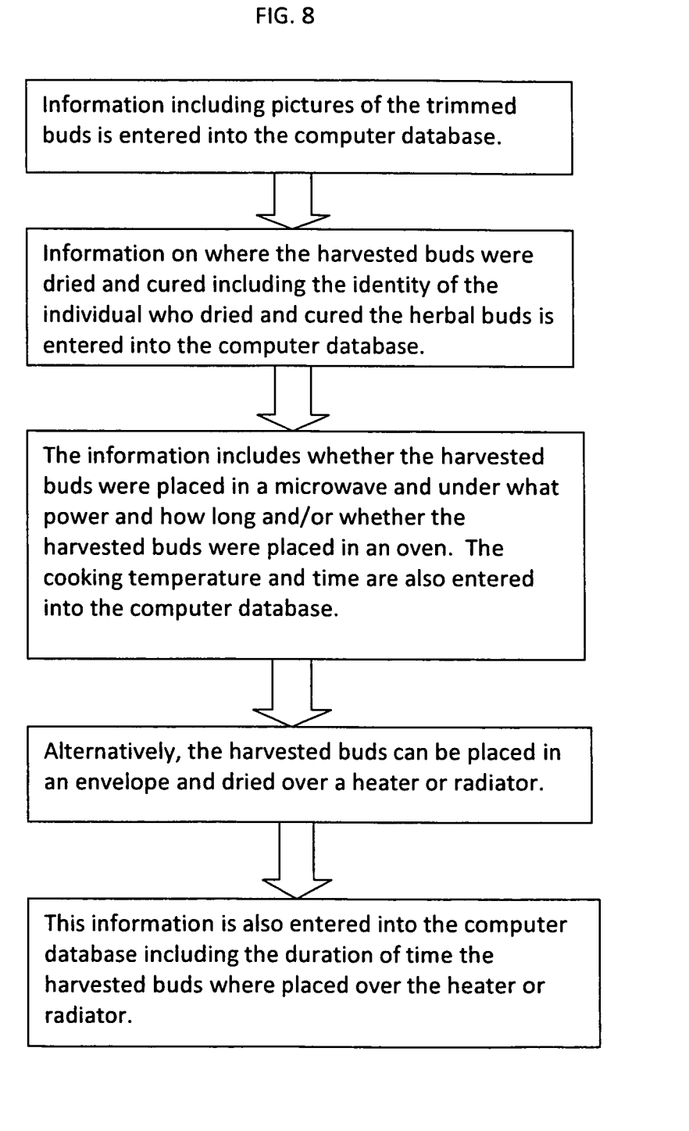
FIG. 8 is block diagram illustrating converting the harvest buds into a medicinal herb.

Referring to FIG. 8, information including pictures of the trimmed buds is entered into the computer database. Information on where the harvested buds were dried and cured including the identity of the individual who dried and cured the herbal buds is entered into the computer database. The information includes whether the harvested buds were placed in a microwave and under what power and how long and/or whether the harvested buds were placed in an oven. The cooking temperature and time are also entered into the computer database. Alternatively, the harvested buds can be placed in an envelope and dried over a heater or radiator. This information is also entered into the computer database including the duration of time the harvested buds where placed over the heater or radiator.

Figure 9:
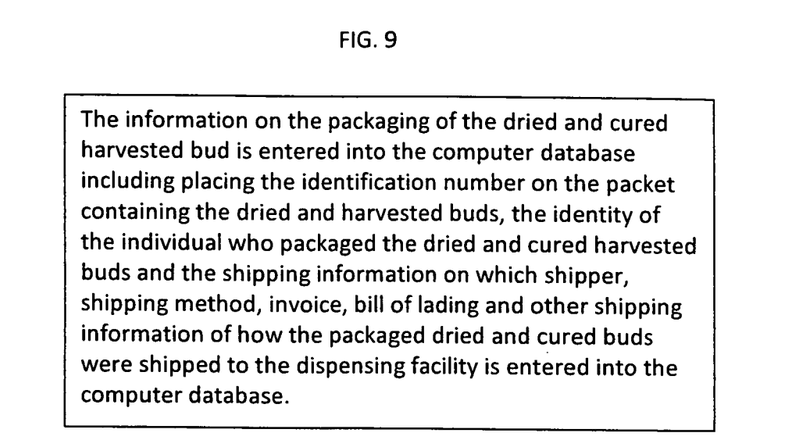
FIG. 9 is a block diagram chain of custody information on shipping the medicinal herb to a dispensing facility.

Referring to FIG. 9, the information on the packaging of the dried and cured harvested bud is entered into the computer database including placing the identification number of the packet containing the dried and harvested buds, the identity of the individual who packaged the dried and cured harvested buds and the shipping information on which shipper, shipping method, invoice, bill of lading and other shipping information about how the packaged dried and cured buds were shipped to the dispensing facility is entered into the computer database.

Figure 10:
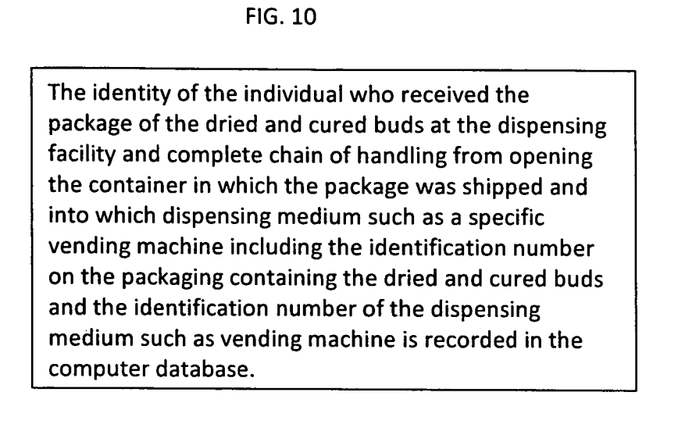
FIG. 10 is a block diagram illustrating the chain of authentication from receipt of the medicinal herb at a dispensing facility to the medicinal herb being dispensed to a person.

Referring to FIG. 10, the identity of the individual who received the package of the dried and cured buds at the dispensing facility and complete chain of handling from opening the container in which the package was shipped and into which dispensing medium such as a specific vending machine including the identification number on the packaging containing the dried and cured buds and the identification number of the dispensing medium such as a vending machine is recorded in the computer database.

Therefore, the present invention provides a complete chain of custody from obtaining the seeds through growing the seeds into a plant and harvesting the medicinal herb buds from the plant and preparing the harvested buds into a medicinal herb and the tracking of all personnel involved through shipping the medicinal herb to the legal dispensing facility and how and where the medicinal herb was dispensed to a patient is fully recorded in the computer database to provide full authentication and verification from seed to dispensed medicinal herb.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A method of authentication and verification of a medicinal herb, consisting of:
   a. utilizing a computer database to receive information and transformation of the information into a verification of a legal origin of the medicinal herb confirming a legal process from initial creation of the medicinal herb to legal sale of the medicinal herb to a person:
   b. obtaining authentication information on where seeds from which a plant to grow the medicinal herb were obtained, including legal seed selling information about the seed grower, the specific type of special variety of plant seed and a written chain of custody from the seed grower to the location where the seeds will be grown into plants which is then entered into a computer database;

c. obtaining information about whether the seeds were feminized seeds to create only female plants or normal seeds creating both female and male plants, which information is entered into the computer database;

d. keeping a computer database record setting forth detailed information about the seed grower, where the seeds were germinated and the shipping documents to confirm the authenticity of the specific seeds including the variety of medicinal herb to be obtained from the seeds;

e. entering into the computer database the name, home address and fingerprint information about an individual or individuals who are given possession of the seeds when the seeds arrive at a cultivation facility to grow the seeds into plants, and inputting information on a packet into which the seeds are placed including a specific seed identification number placed on the packet;

f. obtaining additional information about the soil used to grow the seeds into plants, the type of grow light used and nutrients added to the soil, which information is entered into the computer database;

g. entering into the computer database the location of the cultivation facility and the employees who are in charge of growing the seeds into a plant, the computer database including information about the growing facility, its license to grow the medicinal herb, and the specific greenhouse number where the seeds will be grown into a plant;

h. entering into the computer database information on the identification of the employee who planted the seeds into a pot, a label placed on the pot with a corresponding identification number obtained from the packet into which the seeds were placed when they arrived at the cultivation facility from the seed grower;

i. entering into the computer database growing information setting forth when the plant began to sprout and the rate of growth of the plant, when the plant began to flower and when herbal buds began to form;

j. entering into the computer database the day, date and time of when the herbal buds from the plant were trimmed and harvested, including the identity of the individual who did the harvesting, information about when the plaint was cut and where the herbal buds were removed from the plant;

k. entering into the computer database information including pictures of the trimmed herbal buds, how the harvested buds were dried and cured including the identity of the individual who dried and cured the herbal buds and information on how the herbal buds were treated to become a medicinal herb;

l. entering into the computer database information on the packaging of the dried and cured harvested herbal buds including the corresponding identification number placed on a packet containing the dried and cured herbal buds which have been treated to become the medicinal herb, the identity of the individual who packaged the medicinal herb and the shipping information on which shipper, shipping method, invoice, bill of lading and other shipping information about how the medicinal herb was placed in a container and shipped to a dispensing facility;

m. entering into the computer database the identity of the individual who received the package of the dried and cured buds at the dispensing facility and complete chain of handling from opening the container in which the package was shipped and into which dispensing medium the medicinal herb was placed including the identification number on the packaging containing the medicinal herb and an identification number of the dispensing medium;

n. entering into the computer database the day, date and time the medicinal herb was dispensed to the person; and o. the computer database records and stores all of the information in retrievable form to provide proof of legal growing, processing and sale of the medicinal herb.

2. A method of authentication and verification of a medicinal herb, consisting of:

a. utilizing a computer database to receive information and transformation of the information into a verification of a legal origin of the medicinal herb confirming a legal process from initial creation of the medicinal herb to legal sale of the medicinal herb to a person;

b. obtaining authentication information on where seeds from which a plant to grow the medicinal herb were obtained, including information about the seed grower, and entering into a computer database a written chain of custody from the seed grower to the location where the seeds will be grown into plants;

c. keeping a computer database record setting forth detailed information about shipping documents to confirm the authenticity of the specific seeds including the variety of medicinal herb to be obtained from the seeds;

d. entering into the computer database the personal and fingerprint information about an individual who is given possession of the seeds when the seeds arrive at a cultivation facility to grow the seeds into a plant, and inputting information on a packet into which the seeds are placed including a specific seed identification number placed on the packet;

e. entering into a computer database the location of the cultivation facility and the employees who are in charge of growing the seeds into a plant, the computer database including information about the growing facility, its license to grow the medicinal herb, and the specific greenhouse number where the seeds will be grown into a plant;

f. entering into the computer database information on the identification of the employee who planted the seeds into a pot, a label placed on the pot with a corresponding identification number obtained from the packet into which the seeds were placed when they arrived at the cultivation facility from the seed grower;

g. entering into the computer database growing information on when the plant began to sprout herbal buds and when the herbal buds were harvested, including the identity of the individual who did the harvesting and a chain of custody information of how the herbal buds were converted into a medicinal herb and which individual performed transforming the herbal buds into a medicinal herb;

h. entering into the computer database information on the packaging of the medicinal herb including the corresponding identification number placed on a packet containing the medicinal herb, the identity of the individual who packaged the medicinal herb and shipping from the cultivation facility to a dispensing facility;

i. entering into the computer database the identity of the individual who received the medicinal herb at the dispensing facility and complete chain of handling from opening a container in which the package was shipped and into which dispensing medium the medicinal herb was placed including the identification number on the packaging containing the medicinal herb and an identification number of the dispensing medium;

j. entering into the computer database the day, date and time the medicinal herb was dispensed to the person; and k. the computer database records and stores all of the information in retrievable form to provide proof of legal growing, processing and sale of the medicinal herb.

3. A system consisting of:

a. utilizing a computer database to receive information and transformation of the information into a verification of a legal origin of the medicinal herb confirming a legal process from initial creation of the medicinal herb to legal sale of the medicinal herb to a person:

b. a computer system to monitor and authenticate the creation of a medicinal herb including information on where seeds used to grow a plant containing a medicinal herb buds were obtained from, information on how and where the seeds were grown to cultivate the plant, information on when the buds were harvested from the plant and converted into a medicinal herb;

c. computerized information including a full chain a custody of all personnel involved from obtaining the seeds, cultivating the seeds into a plant, harvesting growth from the plant and converting it into a medicinal herb and transportation of the medicinal herb to a dispensing facility and how the medicinal herb was dispensed to a patient; and d. the computer database records and stores all of the information in retrievable form to provide proof of legal growing, processing and sale of the medicinal herb.

\* \* \* \* \*